United States Patent [19]

Guillaumot

[11] Patent Number: 4,571,741
[45] Date of Patent: Feb. 25, 1986

[54] ERGONOMIC HELMET MEANS

[75] Inventor: Jacques Guillaumot, Fabregue, France

[73] Assignee: Commissariat a l'Energie Atomique, Paris, France

[21] Appl. No.: 686,234

[22] Filed: Dec. 26, 1984

[30] Foreign Application Priority Data

Dec. 27, 1983 [FR] France .................. 83 20849

[51] Int. Cl.⁴ ............................................. A42B 1/00
[52] U.S. Cl. .............................................. 2/8; 2/424; 2/171.3
[58] Field of Search ................. 2/8, 424, 10, 171.3

[56] References Cited

U.S. PATENT DOCUMENTS

| | | |
|---|---|---|
| 2,122,923 | 7/1938 | Yettner . |
| 2,402,820 | 6/1946 | Kitchen ................................ 2/8 X |
| 2,688,962 | 9/1954 | Sommers .............................. 2/8 X |
| 3,540,058 | 11/1970 | LoGuidice ............................. 2/8 |
| 3,649,964 | 3/1972 | Schoelz et al. ........................ 2/8 |
| 3,657,740 | 4/1972 | Cialone ................................. 2/8 |
| 3,692,974 | 9/1972 | Thomason et al. ................ 219/147 |
| 4,227,520 | 10/1980 | Lord ............................... 2/171.3 X |
| 4,293,757 | 10/1981 | Niemi ................................. 2/8 X |

FOREIGN PATENT DOCUMENTS

| | | |
|---|---|---|
| 8031132 | 12/1981 | Fed. Rep. of Germany . |
| 2416694 | 9/1979 | France . |
| 801321 | 9/1958 | United Kingdom . |
| 835200 | 5/1960 | United Kingdom . |

Primary Examiner—Ronald Feldbaum
Attorney, Agent, or Firm—Pearne, Gordon, Sessions, McCoy, Granger & Tilberry

[57] ABSTRACT

The ergonomic helmet means according to the invention comprises a pump equipped with a control system simultaneously ensuring the supply of air to the helmet and the manipulation of the vizor. This control system has an operative position ensuring the lowering of the vizor, its maintenance in the lowered position and normal ventilation, as well as an inoperative position ensuring the raising of the vizor, its maintenance in the raised position and reduced ventilation forming a screen around the operator's face.

Application to the protection of personnel working in a dust atmosphere.

8 Claims, 5 Drawing Figures

4,571,741

ERGONOMIC HELMET MEANS

BACKGROUND OF THE INVENTION

The present invention relates to an ergonomic helmet means, i.e. a lightweight, practical and pleasant-to-wear protective helmet.

When carrying out certain work giving off a large amount of dust or sparks, such as welding, grinding, sand blasting or spraying, it is indispensable for the operator to be protected, particularly his face. The same applies when painting and when spraying pesticides in the agricultural field. A certain number of protective devices are presently available, which can be in the form of retractable helmet means made from polypropylene or PVC with a mica window for welders and grinders. However, they have no ventilation and are relatively unpleasant to wear because they retain heat. In addition, masks or half-masks, optionally provided with filter cartridges, filter masks with protection of the eyes, as well as masks provided with autonomous air supply systems, the air being supplied by an external pump or by a compressed air cylinder also exist. Finally, there are complete, tight ventilated garments or clothing which cover the head, chest or the complete body.

All these equipment suffer from the disadvantage of not simultaneously protecting against harmful effects (dust, vapours or sparks) and ensuring the ergonomic comfort of the operator. This either leads to the wearing of limited equipment with low level protection, but ensuring a certain comfort, or the use of equipment ensuring an effective protection, but which cause rapid fatigue, so that after a time the operators no longer wear such equipment. Moreover, the equipment ensuring effective protection is prejudicial to the work being carried out by the user and they are also onerous, which explains their restricted use.

SUMMARY OF THE INVENTION

The present invention aims at obviating these disadvantages by proposing a lightweight, pleasant-to-wear ergonomic helmet means simultaneously ensuring a good protection against harmful effects and adequate comfort of the operator.

In per se known manner, the helmet means according to the invention comprises a part in the form of a helmet equipped with a vizor displaceable between a lowered position and a raised position, as well as a system for supplying air to this part in the form of a helmet by means of an external air source or supply. According to the invention, the helmet means comprises a control means simultaneously ensuring the ventilation and manipulation of the vizor said control means having an "operating" position simultaneously ensuring the lowering of the vizor and its maintaining in the lowered position, together with the normal ventilation and a "inoperative" position simultaneously ensuring the raising of the vizor and its maintenance in the raised position together with a reduced air admission forming the screen around the operator's face.

According to another feature of the invention, the said control means comprise a pump serving as the external air source, said pump being equipped with a control having an operative position ensuring normal ventilation and an inoperative position ensuring a reduced air admission, said control also ensuring the manipulation of the vizor, a system for the filtration of pollutants equipping the said pump, a flexible pipe connecting the pump to said helmet-shaped part and several flexible hoses connecting the end of the flexible pipe opposite to the pump to a number of outlets.

According to a preferred embodiment, at least one of the flexible hoses issues into the end of a tube having a longitudinal slot, whose width increases on moving away from the end into which issues the flexible hose, thus ensuring a laminar airflow.

According to a first embodiment, one of the flexible hoses issues into a cylinder containing a moving piston connected to one end of a spiral spring cooperating with the vizor.

According to a second embodiment, the ergonomic helmet means according to the invention comprises an electric power supply and an element made from a reverse heat retaining or storing material said element being electrically connected to the power supply and cooperates with the vizor.

In this case, the element made from the inverse heat retaining material is preferably a spiral spring, whereof one end is fixed to the helmet-shaped part and whose other end is fixed to a spindle rotating with respect to the helmet-shaped part and integral with the vizor during said rotation.

According to an interesting feature of the invention, the helmet-shaped part is internally lined with a cork layer and a small radio transmitter - receiver can be incorporated into the helmet-like part.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
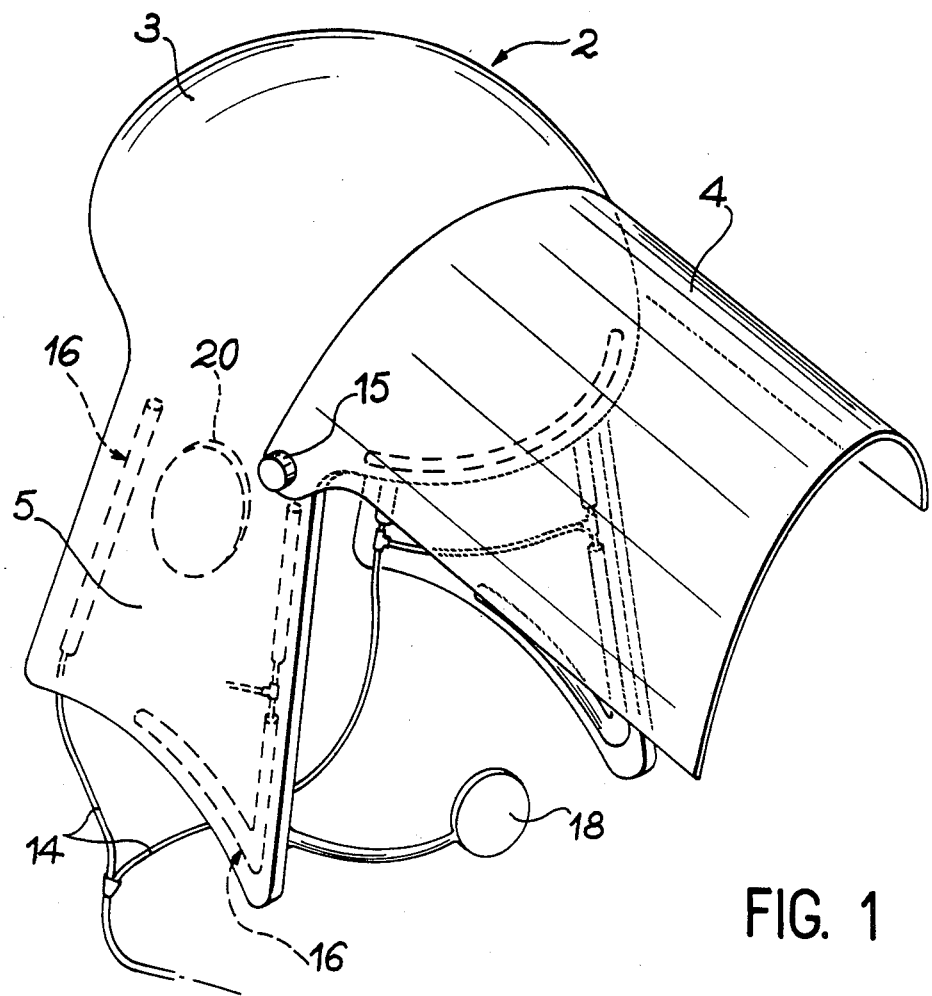
FIG. 1 a diagrammatic perspective view of the ergonomic helmet means according to the invention.
Figure 1:
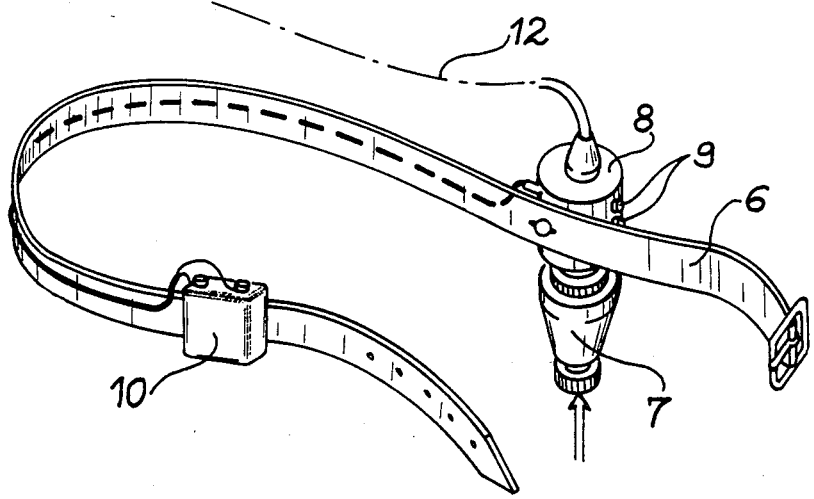

FIG. 1 shows the complete ergonomic helmet means according to the invention, which essentially comprises the helmet-like part 2, on which is mounted a transparent vizor 4 displaceable between a working or lowered position and an inoperataive or raised position, the latter position being illustrated in FIG. 1. The helmet-like part 2 can be made from lightweight carbon fibres or from glass fibres joined by a synthetic glue having good fire resisting characteristics (class M0 or M1). The vizor 4 is advantageously made from synthetic glass with increased alpha and beta ultraviolet radiation protection. It can be semicylindrical, free in its lower portion and articulated in its upper portion to the helmet-shaped part, the vizor 4 being rotatable about a spindle 15.

The means also has a belt 6, worn by the operator, to which is attached an air pump 8, whilst a battery 10 attached to belt 6 applies the electric power to the pump. The latter, which is provided with a filter such as 7, because the helmet means is to be worn in a polluted atmosphere, is connected to the helmet 2 by a flexible pipe 12, whereof the end opposite to pump 8 is connected to two flexible hoses 14, which supply air to different locations in helmet 2, in order to ensure the insulation and ventilation of the operator's face by means of a laminar air flow. The filtering device 7 can e.g. be a PTFE filter, which stops solid aerosols, completed by an active carbon mass which stops organic vapours. It is optionally possible to add a prefilter, if it is necessary to work in a medium containing liquid aerosols. There are two flexible hoses 14, one for each side of the helmet-like part, each of the hoses 14 then being subdivided into a plurality of secondary hoses, as will be explained hereinafter relative to FIG. 2. A certain number of tubes such as 16 are distributed around the helmet 2 in order to ensure ventilation. Pump 8 is equipped with a control means which, in the present embodiment, is in the form of two pushbuttons 9, but can be in any other form, e.g. a single button, knob, handle, etc. The control means 9 has an operative position and an inoperative position. When placed in the operative position, this has the effect of making the pump operate with its normal capacity, so that air is supplied to the different tubes 16 by flexible pipe 12 and hoses 14. In addition, the vizor 4 is lowered into the working position and is maintained in said position by means which will be described hereinafter. When it is placed in the inoperative position, this has the effect of operating the pump at reduced capacity and also of raising the vizor 4 into the inoperative position, where it is maintained. As will be shown in greater detail hereinafter, tubes 16 are arranged in such a way that the ventilation air flows in the form of several air curtains forming a screen around the operator's face, both under normal ventilation and under reduced ventilation conditions. Thus, when vizor 4 is lowered, the interior of the helmet is ventilated and cooled. When the vizor is raised, the reduced ventilation continues to form a screen around the operator's face, which protects it from the ambient atmosphere when he is not working. During rest periods, the respiratory passages are protected from external pollutants (dust, droplets, toxic gases, etc) and by means of air curtains flowing in front of the nose and mouth and towards the chest, which prevents any possible rise of polluting agents.

As can be seen in FIG. 1, the helmet means can be equipped with a radio, which is constituted by a microtransmitter 18 and two earphones 20, the latter being located in the helmet-like part level with the user's ears. It is advantageously possible to use for this purpose the multiplexed radio link means described in French Pat. No. 2,430,143 belonging to the present Applicant. This means permits conversations between each operator and a control station, as well as conversations between the individual operators.

Figure 2:
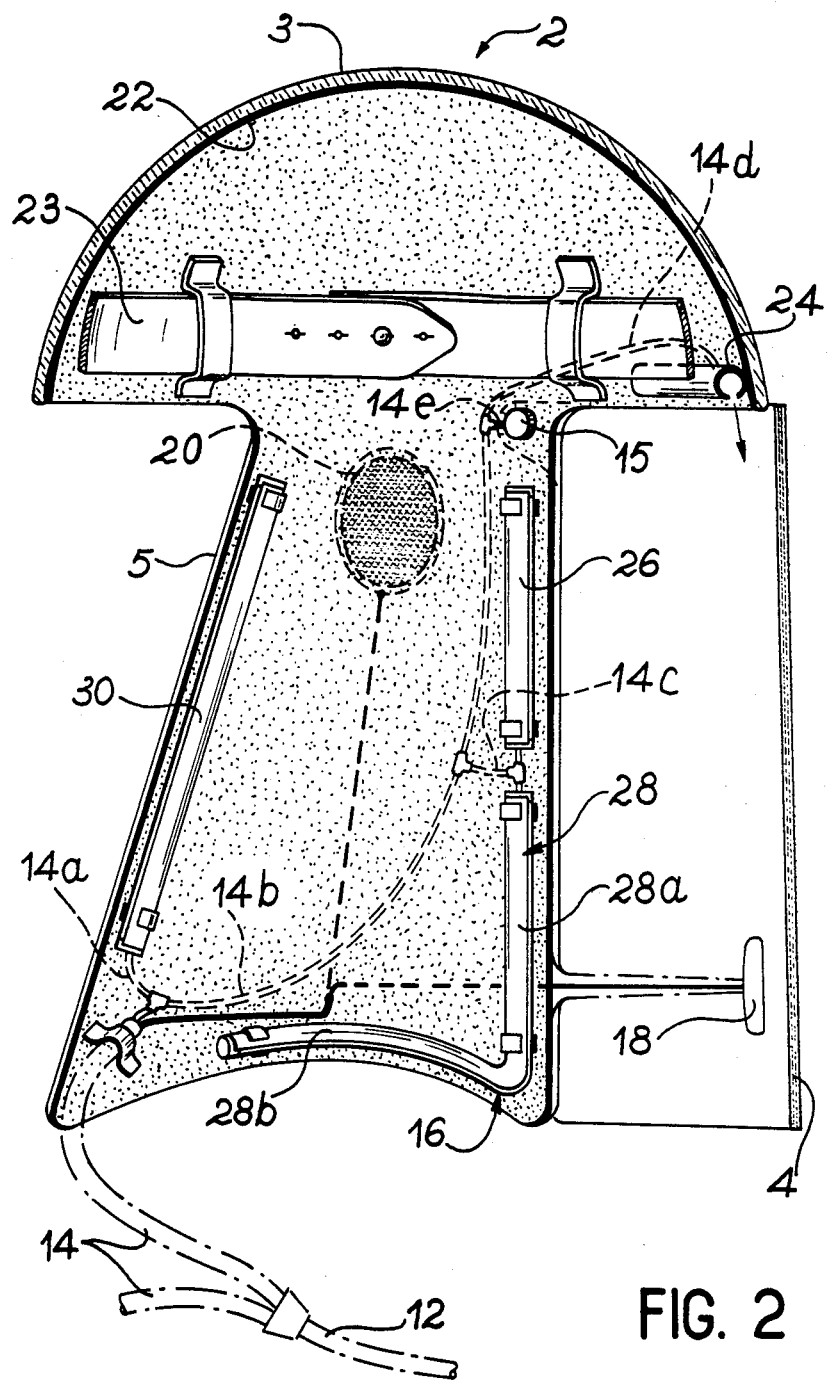
FIG. 2 a sectional view of the helmet-like part of the helmet means.

FIG. 2 is a sectional view through the helmet-like part 2 of the helmet means, where it is possible to see the portions 3 covering the head and 5 protecting the two sides of the operator's head and these portions are internally covered with a cork layer 22 ensuring the sound insulation of the operator and prevents internal humid condensation. Moreover, this cork layer forms a complementary heat shield. A strap 23 makes it possible to adapt the helmet means to the size of the operator's skull. It is also possible to see the earphones 20 of the small radio transmitter - receiver and these are located beneath the cork material.

Figure 3:
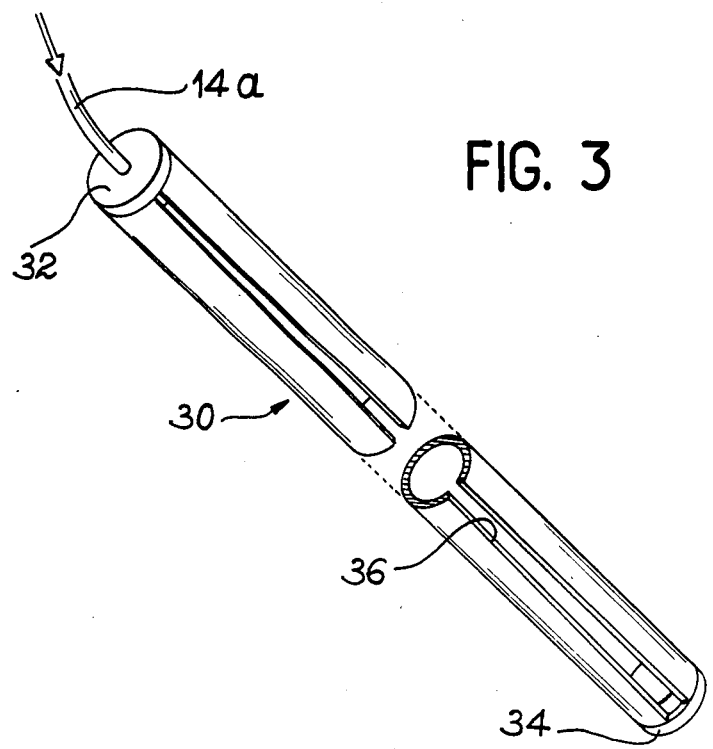
FIG. 3 a diagrammatic perspective view of one of the tubes equipping the helmet-like part, in order to ensure a laminar flow.

FIG. 2 also shows the end of the flexible pipe 12, which issues into the lower portion of helmet 2 and is connected to several flexible hoses which supply air to various outlets. The latter are constituted by slit tubes distributed at different locations of helmet 2, in order to produce a laminar air curtain around the operator's face. In the present embodiment, the tubes are arranged in the following manner. A tube 24 is positioned in front of the user and ensures a downward flow of air, whilst a vertical tube 26 on either side of the face directs the air towards the front thereof. There are two tubes 28, each formed by a vertical portion 28a having the same function as tubes 26 and a lower portion 28b arranged in such a way that the air flows vertically on the user's shoulders and these are located on either side of the helmet, whilst two tubes 30 produce an air curtain to the rear of the operator's face. Hose 14 supplying the helmet 2 shown in FIG. 2 is subdivided into a hose 14a supplying tube 30 and a hose 14b supplying the other tubes. Hose 14b is connected to tubes 26, 28 by hose 14c, to tube 24 by hose 14d and to articulation 15 by hose 14e. This articulation will be described hereinafter relative to FIG. 4. The shape of the tubes can be better gathered from the perspective view of FIG. 3, where it is possible to see that tube 30 is sealed at its two ends by two caps 32, 34, the air arriving at one end of tube 30 from hose 14a, which issues level with cap 32. Tube 30 has a longitudinal slit 36, whose length increases on moving away from the end at which hose 14a issues, i.e. on moving from cap 32 towards cap 34. This arrangement ensures a constant pressure and consequently a constant flow rate at all points of the tube, which provides a laminar flow.

Figure 4:
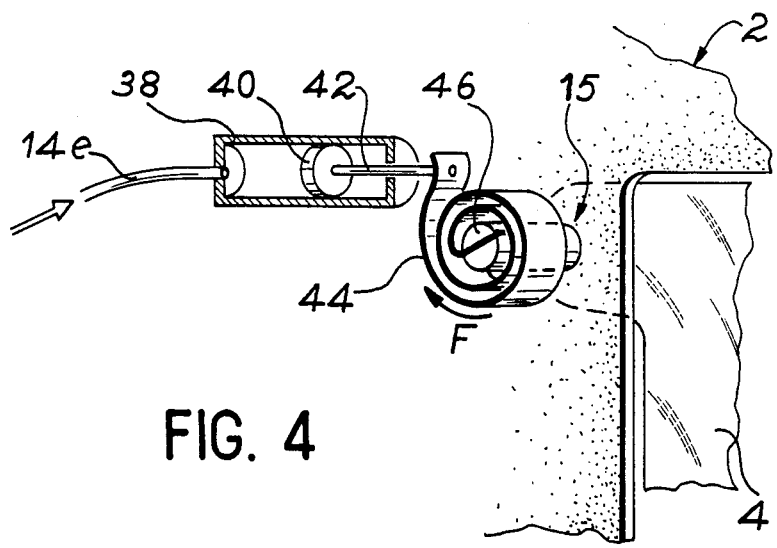
FIG. 4 a diagrammatic view of a first embodiment of the automatic vizor raising and lowering system.

FIG. 4 shows the system for automatically raising the vizor according to the first embodiment, when this is controlled by pneumatic means. In this case, one of the flexible hoses 14e issues into a cylinder 38, within which can move a piston 40. The latter is connected by a rod 42, to one end of a spiral spring 44, whose other end is fixed to a spindle 46, which forms the vizor rotation axis 15. When the control means 9 (FIG. 1) is placed in the operative position, pump 8 ensures a high air flow and consequently a large admission of air and a high pressure in cylinder 38. This has the effect of forcing piston 40 towards the right in the drawing and consequently of compressing spring 44 in the direction of arrow F, i.e. in a clockwise direction in FIG. 4. The rotation of the spring also rotates spindle 46 and consequently vizor 4, whilst maintaining the latter in the lowered or working position whilst the pump is operating, because the latter permanently supplies a high air pressure within cylinder 38. When the control means 9 is placed in the operative position, pump 8 supplies a reduced air flow to helmet 2, so that the pressure within cylinder 38 decreases. Piston 40 then moves towards the left in the drawing under the action of spring 44, which slackens and unwinds in the direction opposite to arrow F, which has the effect of raising vizor 4 and of maintaining the latter in said position, whilst the air pressure is low within cylinder 30.

In another embodiment, it is possible to replace the pneumatic system with cylinder 38 and piston 40 by a device having an element or plate made from a reverse heat retaining or storing material. Thus, certain materials such as e.g. certain nickel and titanium alloys expand if the temperature decreases and contract if the temperature increases. More precisely, these materials resume a shape previously imposed thereto at a certain temperature when they again reach said temperature. Thus, a material can be made to contract instead of expanding on passing from a given temperature to a higher temperature and it is for this reason that reference is made to "reverse heat retention or storing". For example, it is possible to use a plate made from such a material, whereof one end is fixed to the helmet 2 and the other to the end of the spring 44. Through placing the control means of pump 8 in the operative position, electric power is passed into said element, so that it heats and contracts, which has the effect of contracting spring 44 and lowering vizor 40. On placing the control means into the inoperative position, although pump 8 continues to ensure a reduced air flow, the passage of current into the reverse heat storing material element is interrupted, leading to cooling and elongation thereof, so that the vizor rises.

Figure 5:
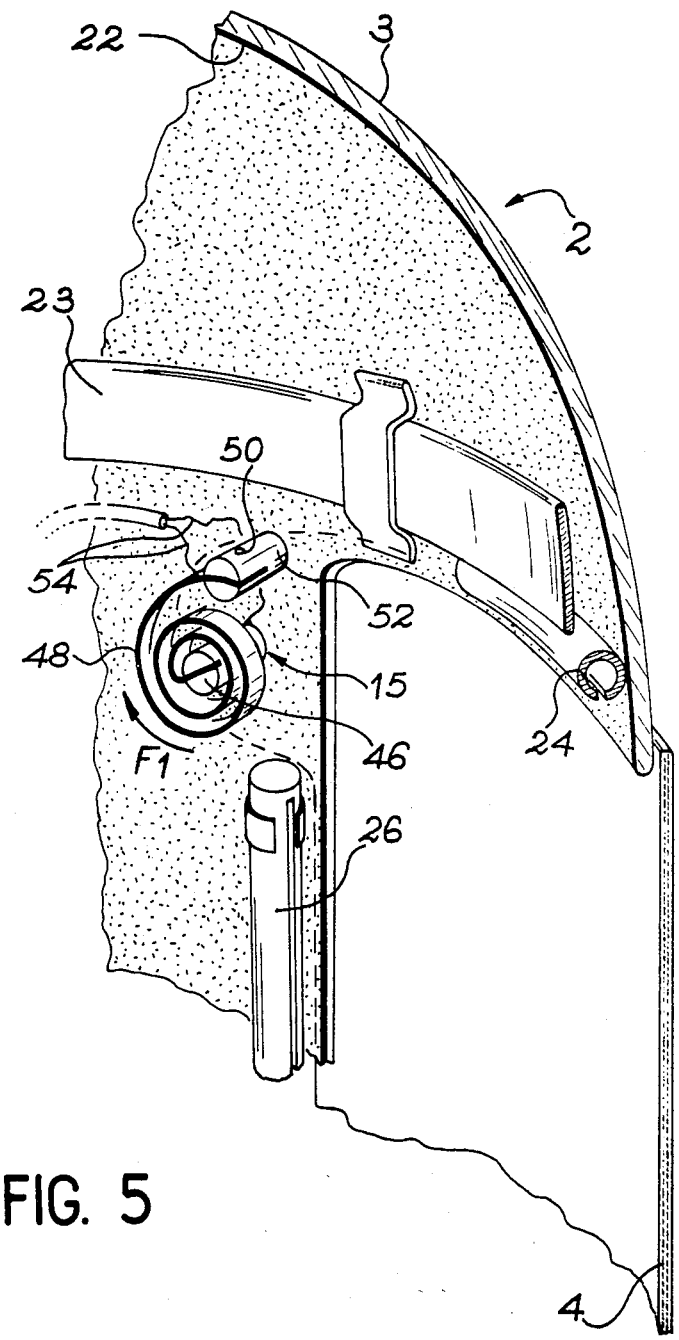
FIG. 5 a view similar to FIG. 4 illustrating a second embodiment of the automatic vizor raising and lowering system using a reverse heat retaining or storing material.

FIG. 5 illustrates another embodiment in which the element made from a reverse heat retaining material is in the form of a spiral spring 48 similar to spring 44 in FIG. 4. One end of spring 44 is fixed to spindle 46, which rotates the vizor. The other end of spring 44 is held by a pin 50 on a support 52, which is fixed with respect to the helmet 2. Finally, two wires 54 in each case connect one end of spring 48 to an electric power supply, e.g. the battery 10 in FIG. 1.

This device functions in the following way. On placing the control means 9 of pump 8 into the operative position, current is supplied to wires 54 and consequently spring 48, the latter heating and therefore contracting. As one end thereof is fixed to support 52, its other end brings about the rotation of spindle 46 in the direction of arrow F1 and vizor 4 is lowered, as shown in FIG. 5. On placing the control means 9 of pump 8 into the inoperative position, the passage of current is interrupted to wires 54 and also spring 48. The latter cools and lengthens, unwinding in the opposite direction to arrow F1 and the rotation of spindle 46 raises vizor 4.

Thus, the invention proposes a particularly interesting ergonomic helmet means, because it is easy to mass-produce and therefore inexpensive. In addition, it is light and pleasant to wear, whilst effectively protecting the user. Moreover, through having a reduced air flow when the pump control is in the inoperative position enables the operator to remain in the polluted area during work breaks, whilst still being protected from the corresponding atmosphere.

What is claimed is:

1. An ergonomic helmet means of the type comprising a helmet-like part equipped with a vizor displaceable between a lowered position and a raised position, as well as a system for supplying air to said helmet-like part by means of an external air source equipped with a control means, wherein the control means simultaneously ensures the ventilation and manipulation of the vizor, said control means having an operative position simultaneously ensuring the lowering of the vizor and its maintenance in its lowered position, together with normal ventilation and an inoperative position simultaneously ensuring the raising of the vizor and its maintenance in the raised position, together with a reduced air admission forming a screen around the operator's face.

2. An ergonomic helmet means according to claim 1, wherein the said control means comprise a pump serving as the external air source, said pump being equipped with a control having an operative position ensuring normal ventilation and an inoperative position ensuring a reduced air admission, said control also ensuring the manipulation of the vizor, a system for the filtration of pollutants equipping the said pump, a flexible pipe connecting the pump to said helmet-shaped part and several flexible hoses connecting the end of the flexible pipe opposite to the pump to a number of outlets.

3. An ergonomic helmet means according to claim 2, wherein at least one of the flexible hoses issues at the end of a tube having a longitudinal slit, whose width increases on moving away from the end at which the flexible tube issues, thus ensuring a laminar air flow.

4. An ergonomic helmet means according to claim 2, wherein at least one of the flexible hoses issues into a cylinder containing a mobile piston connected to one end of a spiral spring, which cooperates with the vizor.

5. An ergonomic helmet means according to claim 2, wherein it comprises an electric power supply and an element made from a reverse heat storing or retaining material, said element being electrically connected to the power supply and cooperating with the vizor.

6. An ergonomic helmet means according to claim 6, wherein the element made from the reverse heat storing material is a spiral spring, whereof one end is fixed to the helmet and whereof the other end is fixed to a spindle, which rotates with respect to the helmet and is integral with the vizor during this rotation.

7. An ergonomic helmet means according to claim 1, wherein the helmet is internally lined with a cork layer.

8. An ergonomic helmet means according to claim 1, wherein it comprises a small radio transmitter - receiver incorporated into the helmet.

* * * * *